(12) United States Patent
Chervinsky

(10) Patent No.: US 9,012,486 B2
(45) Date of Patent: Apr. 21, 2015

(54) TOPICAL COMPOSITION FOR PAIN RELIEF

(76) Inventor: Alex Chervinsky, Brooklyn, NY (US)

( * ) Notice: Subject to any disclaimer, the term of this patent is extended or adjusted under 35 U.S.C. 154(b) by 152 days.

(21) Appl. No.: 13/295,142

(22) Filed: Nov. 14, 2011

(65) Prior Publication Data

US 2013/0123320 A1    May 16, 2013

(51) Int. Cl.
| | |
|---|---|
| A61K 45/06 | (2006.01) |
| A61K 31/135 | (2006.01) |
| A61K 31/167 | (2006.01) |
| A61K 31/192 | (2006.01) |
| A61K 31/195 | (2006.01) |
| A61K 31/197 | (2006.01) |
| A61K 31/4168 | (2006.01) |

(52) U.S. Cl.
CPC .............. *A61K 45/06* (2013.01); *A61K 31/135* (2013.01); *A61K 31/167* (2013.01); *A61K 31/192* (2013.01); *A61K 31/195* (2013.01); *A61K 31/197* (2013.01); *A61K 31/4168* (2013.01)

(58) Field of Classification Search
CPC . A61K 31/135; A61K 31/167; A61K 31/192; A61K 31/195; A61K 31/4168; A61K 31/197
See application file for complete search history.

(56) References Cited

U.S. PATENT DOCUMENTS

| | | | | |
|---|---|---|---|---|
| 5,900,249 | A * | 5/1999 | Smith ........................... | 424/443 |
| 6,147,102 | A * | 11/2000 | Borgman ...................... | 514/392 |
| 6,197,830 | B1 * | 3/2001 | Frome .......................... | 514/654 |
| 2004/0076648 | A1 * | 4/2004 | Williams et al. .............. | 424/400 |
| 2004/0101582 | A1 * | 5/2004 | Wolicki ........................ | 424/760 |
| 2005/0256187 | A1 * | 11/2005 | Liedtke ........................ | 514/506 |
| 2008/0171075 | A1 * | 7/2008 | Ozturk et al. ................. | 424/449 |
| 2010/0226972 | A1 * | 9/2010 | Lutz ............................ | 424/450 |

OTHER PUBLICATIONS

HUMCO PENcream (Copyright 2008; Accessed from http://compounding.storesecured.com/items/bases/pencream-1-lb-601001001-detail.htm on Aug. 5, 2013).*

* cited by examiner

*Primary Examiner* — James D Anderson
(74) *Attorney, Agent, or Firm* — Ted Whitlock

(57) ABSTRACT

Described is a topically applied composition relief of pain. Also described are methods of preparing the composition and methods of using the composition to relieve pain.

7 Claims, No Drawings

TOPICAL COMPOSITION FOR PAIN RELIEF

BACKGROUND OF THE INVENTION

1. Field of the Invention

The present invention relates to compositions and methods for pain relief.

2. Description of the Related Art

Pain results from the noxious stimulation of nerve endings. Nociceptive pain is caused by stimulation of nociceptors (e.g., a needle stick or skin pinch), which then transmit impulses over neural pathways to the spinal neurons and then to the brain. Neuropathic pain is caused by damage to neural structures, such as peripheral nerve endings or nociceptors, which can generate impulses in the absence of stimulation (e.g., herpes zoster pain after the rash has healed).

In contrast to pain treatment with systemic agents, pain can be treated locally by topically administering a pain relieving agent directly to the painful area to block the nociceptive mechanistic pathway. Local anesthetics prevent the generation and conduction of nociceptive nerve impulses. Thus, for example, a local anesthetic or analgesic can be topically applied at the pain area. Advantages of topical anesthetic or analgesic administration over systemic administration of pain relievers include decrease or preclusion of certain side effects, improved patient compliance, and reversible action (i.e., the action can be reversed by removing the anesthetic from the application site).

A variety of drug classes have anesthetic or analgesic properties and can be administered in topical formulations. Traditional local anesthetics or sodium-channel blockers, such as lidocaine prevent the generation and conduction of nerve impulses by decreasing or preventing the large transient increase in the permeability of excitable membranes to Na+. Other agents with analgesic properties include the non-steroidal anti-inflammatories ("NSAIDs") and opioids, such as morphine.

It is common practice to provide a topical pain reliever using the well-known NSAID, salicylic acid (aspirin). Aspirin has been used effectively for many years in the medical and scientific community as a pain reliever. Despite its benefits, systemic administration of aspirin has been shown to cause certain side effects in its users, for example stomach irritation and other internal problems associated with ingesting aspirin.

Applying an aspirin solution topically to a user's skin, thereby avoiding the need for a user to ingest aspirin, has been shown to be an effective manner of gaining the benefits of aspirin without the potential side effects. However, there are difficulties associated with the ability to achieve a safe and stable form of a topical pain reliever containing aspirin that will remain in suspension within the solution of the topical pain reliever.

In view of these difficulties, other NSAIDs have been utilized for their anti-inflammatory or analgesic properties. It is an important aspect of any NSAID-based topical pain reliever to permeate the necessary layers of the integument or skin in order to relieve pain without adversely affecting vital internal organs. Accordingly, it is accepted that an effective topical pain reliever should be in the form that dissolves the analgesic agents and transports it to the area of pain where it can then permeate the integument or skin to provide effective relief.

Topical pain relievers have been introduced in the past, but such topical pain relievers have traditionally had problems of maintaining the analgesic in suspension within the solution of the topical pain reliever. Further, topical pain relievers have been known to have a delayed onset of action after they have been applied to the integument or skin. Several reasons may cause such a result, for example the topical pain reliever may not effectively permeate the skin.

Many patients with localized pain due to arthritis, bursitis, sprain or muscle strain, bruises or hematomas cannot tolerate conventional NSAIDS. In addition, topical administration of conventional NSAIDS has been known to be ineffective because only a therapeutically ineffective amount of the drug can penetrate the skin. In addition, indications such as acne, psoriasis and eczema are typically refractory to topical or oral administration of NSAIDS.

In addition, joint pain can often indicate the onset of a condition called osteoarthritis. Osteoarthritis is a degenerative joint disease affecting articular cartilage developing in the fourth and fifth decades of life that was initially believed to be a disease of wear and tear due to mechanical stress on the joints. It is now known that the pathology of osteoarthritis is not entirely mechanical and involves changes in the joint metabolism. Specifically, altered glucosamine metabolism appears to play a key role in the development of osteoarthritis.

An effective treatment of osteoarthritis must address two types of problems: (i) pain, and joint tenderness, swelling and stiffness must be alleviated as an immediate patient's problem; and (ii) the degenerative process must be stopped preferably at its earlier stages. Treatment with anti-rheumatics and NSAIDs has not proven successful. Anti-rheumatics, although quickly effective, were recently shown to impair the very function that physicians were trying to improve, and anti-inflammatory drugs alleviate the pain but do not address the underlying degenerative disorder.

Therefore, what is needed is a topical composition that provides effective pain relief, is stable for long periods of time and provides a long shelf-life, and avoids the disadvantages associated with other topical analgesics or systemically administered drugs. What is further needed is a composition that is effective in treating a wide variety of inflammatory conditions by topical application of the composition.

These advantageous properties are provided by the composition set forth in the description that follows. Further advantages will be apparent from the description, or may be realized by the practice of the invention without undue experimentation.

SUMMARY OF THE INVENTION

The subject invention concerns a composition which can be topically applied to the skin for the relief of pain at the site of application. An embodiment of a composition according to the invention comprises an effective amount of at least one anti-spasmodic or GABA-agonist, at least one local anesthetic agent, at least one $\alpha_2$-adrenergic agonist, at least one NMDA-receptor antagonist, at least one Non-Steroidal Anti-inflammatory Drug (NSAID), at least one serotonin-norepinephrine reuptake inhibitor (SNRI), together with a solvent in a cream or ointment base.

A preferred embodiment for the composition of the subject invention comprises, in a cream or ointment base (inactive pharmaceutical compounding base):

about 1-20% anti-spasmodic or GABA-agonist
    about 1-5% local anesthetic agent
    about 0.1-1.0% $\alpha_2$-adrenergic agonist
    about 1-20% NMDA-receptor antagonist
    about 1-20% Non-Steroidal Anti-inflammatory Drug (NSAID)
    about 1-10% Serotonin-Norepinephrine Reuptake Inhibitor (SNRI), and
    about 1-10% solvent.

The cream or ointment pharmaceutical compounding base can comprise about 25% to about 75% (w/w) of the composition, and preferably comprises about 50% to about 60% of the composition.

In a more preferred embodiment, the subject composition comprises, in a cream or ointment base:
 gabapentin—1-10% (anti-spasmodic or GABA-agonist
 baclofen—1-10% (anti-spasmodic or GABA-agonist)
 lidocaine HCl—1-10% (local anesthetic agent)
 clonidine HCl—0.1-1.0% ($\alpha_2$-adrenergic agonist)
 ketamine HCl—1-20% (NMDA-receptor antagonist)
 ketoprofen—1-20% (NSAID)
 amitriptyline HCl—1-10% (SNRI)
 DMSO—1-10% (solvent)

The above ingredients are preferably mixed with or into a pharmaceutical compounding base, such as PENcream, which makes up the balance of the composition, and typically comprises about 50-60% of the composition.

In a most preferred embodiment, a composition of the subject invention comprises:
 gabapentin—5%
 baclofen—4%
 lidocaine—5%
 clonidine—0.2%
 ketamine—10%
 ketoprofen—10%
 amitriptyline—2%
 DMSO—5%
 PENcream base—58.8%

The subject invention further comprises a method of preparing the disclosed embodiments of the composition. For example, the process comprises the following steps:
1. adding all active pharmaceutical ingredients (APIs) in a single vessel;
2. adding to the APIs about 75% of the final amount of compounding base;
3. adding the solvent (e.g., DMSO) to the APIs in 75% compounding base;
4. mixing the APIs in 75% compounding base and solvent for about 2 minutes using a mixer at relatively high speed (e.g., level 9 of 10);
5. adding the remaining about 25% of the compounding base to form a final mixture;
6. mixing the final mixture using a mixer until the mixture is substantially homogenous, typically for about 7 minutes at high speed (level 9 of 10).

The subject invention further comprises a method of using the composition, for example, topically applying a safe and effective amount of the composition to the skin for the treatment of pain caused by joint stiffness, arthritis, swelling, Inflammation or edema, muscle cramps or tremors, or for relief of discomfort from sensations such as a "burning" sensation or pain, or unspecified tingling sensations in limbs or hands or feet. An effective amount is typically an amount to cover the area experiencing the pain or sensation.

It is therefore an object of the present invention to provide a composition and method for the topical or transdermal relief of pain to provide immediate, long-lasting and cumulative relief from pain and inflammation of sore or stressed muscles and joints.

It is yet another object of the present invention to provide a pain relief composition comprising a plurality of Active Pharmaceutical Ingredients, which is effective and comfortable to apply to the skin.

It is yet another object of the present invention to provide a soothing, anti-inflammatory complex for the joints and muscles, which can be used in combination with other pain relief agents.

Other objects and advantages of the present invention will be apparent from a review of the following specification.

DETAILED DESCRIPTION

The detailed description set forth below is intended as a description of exemplary embodiments and is not intended to represent the only forms in which the exemplary embodiments may be constructed and/or utilized. The description sets forth the functions and the sequence of steps for preparation and/or use of the exemplary embodiments. However, it is to be understood that the same or equivalent functions and sequences which may be accomplished by different exemplary methods are also intended to be encompassed within the spirit and scope of the invention.

As used herein, "safe and effective amount" means a sufficient amount of a compound, composition or other material described by this phrase to significantly induce a positive modification in the condition being treated, but low enough to avoid undue side effects (e.g., significant skin irritation or sensitization), within the scope of sound judgment of the skilled person. The safe and effective amount of the compound, composition or other material may vary with the particular person being treated, factoring the age and physical condition of the biological subject being treated, the severity of the condition, the duration of treatment, the nature of concurrent therapy, the specific compound, composition, or other material employed, the particular carrier utilized, and the factors within the knowledge and expertise of the skilled person.

A composition according to the subject invention comprises the following active pharmaceutical ingredients (APIs):
1. At least one anti-spasmodic or GABA-agonist. A preferred embodiment of the subject composition comprises two anti-spasmodic or GABA-agonist APIs, most preferably gabapentin and baclofen. Gabapentin powder and baclofen, USP, are available commercially from Medisca (Plattsburg, N.Y.). Examples of other anti-spasmodics or GABA-agonists that can be used in a composition of the subject invention include, but are not limited to: Acamprosate, Picamilon, GHB, benzodiazepines, nonbenzodiazepines (e.g., Zolpidem, Zopiclone, Zaleplon), barbiturates, methaqualone, muscimol, progabide, and tiagabine, or salts, derivatives, isomers, polymorphs, or esters thereof.
2. At least one local anesthetic agent. A preferred embodiment of the subject composition comprises lidocaine, more preferably lidocaine HCl monohydrate, in the form of a solid powder as a local anesthetic component of the subject composition. Lidocaine HCl monohydrate is commercially available from Medisca (Plattsburg, N.Y.). Examples of other local anesthetics that can be used in a composition of the subject invention include, but are not limited to: local anesthetic esters, selected from the group Procaine, Benzocaine, Chloroprocaine, Cocaine, Cyclomethycaine, Dimethocaine/Larocaine, Piperocaine, Propoxycaine, Procaine/Novocaine, Proparacaine. and Tetracaine/Amethocaine; local anesthetic Amides, selected from the group Articaine, Bupivacaine, Cinchocaine/Dibucaine, Etidocaine, Levobupivacaine, Lidocaine/Lignocaine, Mepivacaine, Prilocaine, Ropivacaine, Trimecaine; salts, derivatives, isomers, polymorphs, or esters thereof, or combinations thereof.

3. At least one $\alpha_2$-adrenergic agonist. A preferred embodiment of the subject composition comprises clonidine, preferably clonidine HCl as an $\alpha_2$-adrenergic agonist component of the subject composition. Clonidine HCl, USP, is commercially available from Medisca (Plattsburg, N.Y.). Examples of other $\alpha_2$-adrenergic agonists that can be used in accordance with the subject composition include, but are not limited to: Guanfacine, Guanabenz, Guanoxabenz (a metabolite of guanabenz), Guanethidine, Xylazine, Tizanidine, Methyldopa, and Fadolmidine, or the salts, derivatives, isomers, polymorphs, or esters thereof. Other agents that classified as $\alpha$-adrenergic agonists but which have not been determined as $\alpha_1$- or $\alpha_2$-adrenergic agonists include: amidephrine, amitraz, anisodamine, apraclonidine, brimonidine, cirazoline, detomidine, dexmedetomidine, epinephrine, ergotamine, etilefrine, indanidine, lofexidine, medetomidine, mephentermine, metaraminol, methoxamine, mivazerol, naphazoline, norepinephrine, norfenefrine, octopamine, oxymetazoline, phenylpropanolamine, rilmenidine, romifidine, synephrine, talipexole, and tizanidine, or salts, derivatives, isomers, polymorphs, or esters thereof. To the extent these agents are identified as $\alpha_2$-adrenergic agonists, they may be substituted for clonidine HCl in a composition of the subject invention.

4. At least one NMDA-receptor antagonist. A preferred embodiment of the subject composition comprises ketamine, preferably ketamine HCl as an NMDA-receptor antagonist component of the subject composition. Ketamine HCl, USP, is commercially available from Medisca (Plattsburg, N.Y.). Examples of other NMDA-receptor antagonists that can be used in accordance with the subject composition include, but are not limited to: Amantadine, Phencyclidine (PCP), Dextromethorphan or dextrorphan, Memantine, Riluzole, HU-211 (also a cannabinoid), Conantokins, or the dual opioids and NMDA-Antagonists: Ketobemidone, Methadone, Dextropropoxyphene, Tramadol, Kratom alkaloids, or Ibogaine. These compounds can also be used as the salts, derivatives, isomers, polymorphs, or esters thereof.

5. At least one Non-Steroidal Anti-inflammatory Drug (NSAID). A preferred embodiment of the subject composition comprises ketoprofen, preferably ketoprofen HCl as an NMDA-receptor antagonist component of the subject composition. Ketoprofen HCl, USP, is commercially available from Letco Medical (Decatur, Ala.). Examples of other NSAIDs that can be used in accordance with the subject composition include, but are not limited to: the Salicylates—aspirin (acetylsalicylic acid), Diflunisal, or Salsalate; the p-amino phenol derivatives—Paracetamol, or phenacetin; the Propionic acid derivatives—ibuprofen, Naproxen, Fenoprofen, Flurbiprofen, Oxaprozin, or Loxoprofen; the Acetic acid derivatives—indomethacin, Sulindac, Etodolac, Ketorolac, Diclofenac, or Nabumetone; theEnolic acid (Oxicam) derivatives—piroxicam, Meloxicam, Tenoxicam, Droxicam, Lornoxicam, or Isoxicam; the Fenamic acid derivatives (Fenamates)—mefenamic acid, Meclofenamic acid, Flufenamic acid, or Tolfenamic acid; the Selective COX-2 inhibitors (Coxibs)—celecoxib, Parecoxib, or Firocoxib; or salts, derivatives, isomers, polymorphs, or esters thereof.

6. At least one serotonin-norepinephrine reuptake inhibitor (SNRI). A preferred embodiment of the subject composition comprises amitriptyline, preferably amitriptyline HCl as an SNRI component of the subject composition. Amitriptyline HCl, USP, is commercially available from Medisca (Plattsburg, N.Y.). Examples of other SNRIs s that can be used in accordance with the subject composition include, but are not limited to: Venlafaxine, Desvenlafaxine, Duloxetine, Milnacipran, Levomilnacipran, Sibutramine, and Edivoxetine, or salts, derivatives, isomers, polymorphs, or esters thereof.

The subject composition further includes a solvent. Preferably a polar aprotic solvent, such as Dimethyl Sulfoxide (DMSO) can be used in the composition of the subject invention. DMSO is commercially available from Medisca (Plattsburg, N.Y.). Other polar aprotic solvents in this class include dimethylformamide, dimethylacetamide, N-methyl-2-pyrrolidone, and HMPA.

The active components (1.-6., listed above) and solvent are formulated in a pharmaceutical compounding base, such as PENcream. PENcream is commercially available from HUMCO (Texarkana, Tex.). Pharmaceutical compounding bases are well known in the art, and other pharmaceutical compounding bases may be freely substituted for PENcream.

A topical composition prepared in accordance with the present invention may comprise other skin benefiting or carrier components, including, but not limited to conditioning agents, skin protectants, antioxidants, viscosity modifying agents, film formers, emollients, surfactants, solubilizing agents, preservatives, fragrance, chelating agents, foaming or antifoaming agents, opacifying agents, stabilizing agents, pH adjustors, absorbents, anti-caking agents, slip modifiers, various solvents, solubilizing agents, denaturants, bulking agents, emulsion stabilizing agents, suspending agents, colorants, binders, conditioning agent-emollients, surfactant emulsifying agents, biological products, cosmetic soothing aids, and/or combinations thereof.

Emollients that can be used in the subject composition include, but are not limited to, the following:
1. Triglyceride esters which include, but are not limited to, vegetable and animal fats and oils such as palm oil, castor oil, cocoa butter, safflower oil, cottonseed oil, corn oil, olive oil, cod liver oil, almond oil, avocado oil, palm oil, sesame oil, squalene, kikui oil and soybean oil;
2. Acetoglyceride esters, including but not limited to acetylated monoglycerides;
3. Ethoxylated glycerides such as ethoxylated glyceryl monostearate;
4. Alkyl esters of fatty acids having 10 to 20 carbon atoms which include, but are not limited to, methyl, isopropyl and butyl esters of fatty acids;
5. Alkenyl esters of fatty acids having 10 to 20 carbon atoms such as oleyl myristate, oleyl stearate, and oleyl oleate;
6. Fatty acids having 10 to 20 carbon atoms such as pelargonic, lauric, myristic, palmitic, stearic, isostearic, hydroxystearic, oleic, linoleic, ricinoleic, arachidic, behenic, and erucic acids;
7. Fatty alcohols having 10 to 20 carbon atoms such as lauryl, myristyl, cetyl, hexadecyl, stearyl, isostearyl, hydroxystearyl, oleyl, ricinoleyl, behenyl, erucyl, and 2-octyl dodecanyl alcohols;
8. Lanolin and lanolin derivatives including, but not limited to lanolin, lanolin oil, lanolin wax, lanolin alcohols, lanolin fatty acids, isopropyl lanolate, ethoxylated cholesterol and lanolin alcohols;

9. Polyhydric alcohol esters, including but not limited to, ethylene glycol mono and di-fatty acid esters, diethylene glycol mono- and di-fatty acid esters and polyethylene glycol (200-6000) mono- and di-fatty acid esters;
10. Wax esters such as beeswax, spermaceti, myristyl myristate, stearyl stearate;
11. Beeswax derivatives including but not limited to, polyoxyethylene sorbitol beeswax;
12. Vegetable waxes including, but not limited to, carnauba and candelilla waxes;
13. Phospholipids such as lecithin and derivatives;
14. Sterols including, but not limited to, cholesterol and cholesterol fatty acid esters; and
15. Amides such as fatty acid amides, ethoxylated fatty acid amides, and solid fatty acid alkanolamides.

In the manufacture of a preferred embodiment of a composition of the subject invention, a formulation includes:
Gabapentin powder—22.7 g
Baclofen, USP, powder—18.16 g
Lidocaine HCl monohydrate, USP—22.7 g
Clonidine HCl, USP—0.908 g
Ketamine HCl monohydrate, USP powder—45.4 g
Ketoprofen USP powder—45.4 g
Amitriptyline HCl, USP—9.08 g
DMSO (reagent grade) ACS liquid—22.7 ml, and
PENcream base—266.952 g.

The above components are weighed and each of the pre-weighed active ingredient powders (gabapentin, baclofen, lidocaine, clonidine, ketamine, ketoprofen, and amitriptyline) are added to a mixing vessel for a commercial mixer. About 75% of the pre-weighed PENcream compounding base (approximately 200 g), and the entire amount of the DMSO solvent, is added to the active ingredient powders in the mixing vessel. The active ingredient powders, solvent and compounding base are mixed for about 2 minutes at a mixing speed level of 9. The remaining 25% of the compounding base (approximately 67 g) is then added to provide a final mixture. The final mixture is mixed for about 7 minutes at a mixing speed level of 9 until the final mixture is substantially homogeneous, forming the final composition.

A preferred embodiment of the final composition comprises, in weight percent: gabapentin—5%; baclofen—4%; lidocaine—5%; clonidine—0.2%; ketamine—10%; ketoprofen—10%; amitriptyline—2%; DMSO—5%, and PENcream base—58.8%.

The final composition can then be placed into an appropriate container and/or packaging for shipping and storage. The packaging can include listings of ingredients and instructions for use.

A composition according to the subject invention can be topically applied. Typically, a safe and effective amount of the composition is applied to the skin for the treatment of pain caused by joint stiffness, arthritis, swelling, Inflammation or edema, muscle cramps or tremors, or for relief of discomfort from sensations such as a "burning" sensation or pain, or unspecified tingling sensations in limbs or hands or feet. A safe and effective amount is typically an amount (1-5 g) which can be spread onto and cover the specific area experiencing the pain or sensation.

The invention claimed is:

1. A topical composition for pain relief, said composition consisting of:
   about 5% gabapentin;
   about 4% baclofen;
   about 5% lidocaine;
   about 0.2% clonidine;
   about 10% ketamine;
   about 10% ketoprofen;
   about 2% amitryptiline;
   about 5% DMSO; and
   about 58.8% inactive pharmaceutical compounding base.

2. The topical composition of claim 1, wherein said lidocaine is lidocaine HCl monohydrate.

3. The topical composition of claim 1, wherein said clonidine is clonidine HCl.

4. The topical composition of claim 1, wherein said ketamine is ketamine HCl monohydrate.

5. The topical composition of claim 1, wherein the amitriptyline is amitriptyline HCl.

6. A method for relieving pain, said method comprising:
   providing a topical composition of claim 1,
   topically applying an effective amount of said composition to the skin at a site of pain or discomfort, and
   optionally, repeating as needed.

7. A method of preparing a composition of claim 1, wherein said method comprises the steps of:
   pre-weighing or pre-measuring
      Gabapentin powder—22.7 g;
      Baclofen, USP, powder—18.16 g;
      Lidocaine HCl monohydrate, USP—22.7 g;
      Clonidine HCl, USP—0.908 g;
      Ketamine HCl monohydrate, USP powder—45.4 g;
      Ketoprofen USP powder—45.4 g;
      Amitriptyline HCl, USP—9.08 g;
      DMSO (reagent grade) ACS liquid—22.7 ml, and
      inactive pharmaceutical compounding base—266.952 g;
   adding to a mixing vessel the pre-weighed Gabapentin powder, Baclofen powder, Lidocaine HCl monohydrate, Clonidine HCl, Ketamine HCl monohydrate, Ketoprofen powder, and Amitriptyline HCl, with about 75% of the pre-weighed pharmaceutical compounding base and 100% of the pre-measured DMSO;
   mixing for about 2 minutes to form a mixture;
   adding a remaining about 25% of said compounding base to said mixture, and
   mixing for about 7 minutes to form a homogeneous final mixture.

* * * * *